United States Patent
Caers et al.

(10) Patent No.: US 7,667,080 B2
(45) Date of Patent: Feb. 23, 2010

(54) MIXTURES OF C8-C10 ALCOHOLS

(75) Inventors: Raphael Frans Caers, Edegem (BE); Allen David Godwin, Seabrook, TX (US); Mauritz Marie Kelchtermans, Leefdaal (BE); Jean-Jacques G. Muls, Wemmel (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/632,446

(22) PCT Filed: Jul. 14, 2005

(86) PCT No.: PCT/EP2005/007725

§ 371 (c)(1),
(2), (4) Date: Jan. 12, 2007

(87) PCT Pub. No.: WO2006/012989

PCT Pub. Date: Feb. 9, 2006

(65) Prior Publication Data

US 2007/0235687 A1    Oct. 11, 2007

Related U.S. Application Data

(60) Provisional application No. 60/598,639, filed on Aug. 4, 2004.

(51) Int. Cl.
*C07C 31/125* (2006.01)

(52) U.S. Cl. .................................................. 568/840

(58) Field of Classification Search ....................... None
See application file for complete search history.

(56) References Cited

U.S. PATENT DOCUMENTS

| | | | | |
|---|---|---|---|---|
| 4,291,127 | A | 9/1981 | Akabayashi et al. | 560/76 |
| 4,623,748 | A | 11/1986 | Johnson | 560/204 |
| 5,849,960 | A | 12/1998 | Singleton et al. | 568/909 |
| 6,355,711 | B1 | 3/2002 | Godwin et al. | 524/285 |
| 6,437,170 | B1 | 8/2002 | Thil et al. | 560/76 |
| 6,657,092 | B2 * | 12/2003 | Dirkzwager et al. | 568/909 |

FOREIGN PATENT DOCUMENTS

| | | |
|---|---|---|
| EP | 0 278 407 | 8/1988 |
| GB | 1 114 379 | 5/1968 |
| GB | 1 330 112 | 9/1973 |
| WO | WO 92/13818 | 8/1992 |
| WO | WO 03/029180 | 4/2003 |

* cited by examiner

*Primary Examiner*—Daniel M Sullivan
*Assistant Examiner*—Yevegeny Valenrod
(74) *Attorney, Agent, or Firm*—Andrew B. Griffis; Leandro Arechederra, III

(57) ABSTRACT

Mixtures of $C_{8-10}$ primary alcohols, preferably $C_9$ alcohol rich, comprise from 15 to 70 wt. % unbranched molecules, the balance being branched molecules having an average branchiness of at most 2.00 branches per molecule, at least 80% of the ranches being methyl branches and at least 50% of the branched molecules being mono-methyl branched. Plasticiser esters and surfactant derivatives derived from these alcohol mixtures are also provided. The alcohol mixtures are preferably produced by hydroformylation of octene rich streams formed by Fischer-Tropsch synthesis.

11 Claims, No Drawings

MIXTURES OF C8-C10 ALCOHOLS

CROSS REFERENCE TO RELATED APPLICATIONS

This application is a 371 National Stage Application of International Application No. PCT/EP2005/007725, filed Jul. 14, 2005, which claims the benefit of Provisional Application No. 60/598,639, filed Aug. 4, 2004, the disclosures of which are herein incorporated by reference in their entireties.

FIELD OF THE INVENTION

The present invention relates to improvements in or relating to mixtures of $C_{8-10}$ primary alcohols, the mixtures being preferably $C_9$ rich. The invention further relates to the use of the improved alcohol mixtures in the production of esters and in particular plasticiser esters based on polycarboxylic acids or anhydrides and in the esters so produced.

BACKGROUND OF THE INVENTION

Long chain primary alcohols e.g. $C_8$, $C_9$ and $C_{10}$ alcohols are widely used for producing plasticisers. For this, the alcohols are reacted with polycarboxylic acids, such as phthalic acid and adipic acid, forming the corresponding esters. Commercially important examples include adipates of $C_8$, $C_9$ and $C_{10}$ alcohols, for example di(2-ethylhexyl)adipate, diisononyl adipates and diisodecyl adipates; and phthalates of $C_8$, $C_9$ and $C_{10}$ alcohols, such as di(2-ethylhexyl)phthalate, diisononyl phthalates and diisodecyl phthalates.

Diisononyl phthalates are general purpose plasticisers for polyvinyl chloride (PVC), and are used in almost all known flexible PVC applications, both via plastisols and dry blends. Typical applications include those in toys, films, shoes, coatings, floor coverings, gloves, wallpaper, synthetic leather, sealants, tarpaulins, car underbody coatings, upholstery, foamed mats, and sound deadening panels, all based on plasticised PVC. They are also used for producing PVC cable sheathing and insulation, and other calendered flexible PVC products.

Diisononyl adipates are used especially in films, and at lower levels in other products such as wallpaper, synthetic leather, car underbody coatings, gloves, and sealants based on plasticised PVC. Diisononyl adipates are used in particular when the products are intended to be used at low temperatures and/or when plastisols are used as process intermediates.

GB-A-1,330,112 discloses the use of isononanols in the formation of diisononyl esters of phthalic acid or adipic acid as plasticisers where the isononanols have been prepared from 2-ethyl-1-hexene in a known manner by the oxo synthesis by reaction with carbon monoxide and hydrogen at elevated temperature and pressure in the presence of carbonyl complexes of metals of the $8^{th}$ transition group of the Periodic Table, if desired followed by hydrogenation. Because of the branched feedstock, the product alcohol does not contain n-nonanol. The 2-ethyl-1-hexene is obtainable by dimerising 1-butene with trialkyl aluminium compounds. The diisononyl esters described are said to be suitable plasticisers for polyvinyl chloride and to have low volatility, low viscosity and to give good low temperature resistance in the polyvinyl chloride compositions plasticised therewith.

U.S. Pat. No. 4,623,748 describes dialkyl adipates, inter alia diisononyl adipates, prepared by reacting propylene oligomers or butylene oligomers from the dimersol process in the presence of supported tantalum (V) halide/oxide as catalysts, reacting the resultant $C_8$, $C_9$ or $C_{12}$ olefins to give $C_9$, $C_{10}$, or respectively $C_{13}$ alcohols and esterifying these alcohols with adipic acid. The dialkyl adipates are said to have high flash points and to be suitable for use as lubricants.

GB-A-1,114,379 discloses an isomeric nonanols mixture which comprises n-nonanol and includes essentially no alcohols having more than one branch in their carbon skeleton. The mixture is prepared by hydroformylating an octene fraction obtained by polymerizing ethylene with trialkylaluminium catalysts and reducing the hydroformylation product.

WO 92/13818 describes the preparation of diisononyl phthalates starting from butenes and where appropriate, from olefin mixtures comprising propene. The starting materials are oligomerised over supported phosphoric acid catalysts at reaction temperatures of from 200 to 235° C. to give essentially octene-containing olefin mixtures. These octene-containing olefin mixtures are hydroformylated and subsequently hydrogenated to give essentially alcohols mixtures comprising isononanols. These isononanol containing alcohol mixtures are esterified with phthalic anhydride to produce ester mixtures essentially comprising diisononyl phthalates suitable as plasticisers for PVC.

U.S. Pat. No. 4,291,127 describes phthalates of $C_9$ alcohols obtained by an oxo reaction of $C_8$ olefins, hydrogenation of the reaction product and esterification of the $C_9$ alcohols using phthalic anhydride. From 3 to 20% of the $C_8$ olefins have an isobutene skeleton in each molecular chain and less than 3% of the olefins have a quaternary carbon and also more than 90% of the total amount of the $C_8$ olefins are present in the form of n-octenes, monomethylheptenes and dimethylhexenes. The C9 alcohols contain from 2 to 6 wt % n-nonanol. The $C_9$ phthalates are intended to be suitable as plasticisers for PVC.

EP-B-0278407 describes a $C_9$ alcohol mixture for the manufacture of plasticisers which comprises certain proportions of components with a specified GC retention behavior in relation to certain reference compounds. Plasticisers based on the $C_9$ alcohol mixture are intended to give advantageous resistance to low temperatures and good electrical insulation properties.

U.S. Pat. No. 6,355,711 describes plasticiser esters prepared from a $C_9$ oxo alcohol mixture which is 6% straight chain, 74% mono-branched, 20% dibranched and less than 1% tri-branched, the alcohol being derived from an olefin having at least 50% methyl branching at the beta carbon atom.

U.S. Pat. No. 6,437,170 describes mixtures of isononanols and their diesters of adipic or phthalic acid which have defined area signal ratios in the $^1$H NMR spectrum. Reference to isononanols relates to mixtures that are low in unbranched materials.

WO 03/029180 relates to phthalic acid dialkyl ester mixtures including dinonylphthalate isomer mixtures whose viscosity is controlled by the composition of the isomerically pure alcohols from which the mixture can be made. The tables in WO 03/029180 set out several different blends of nonanol isomers and the viscosity of the diisononyl phthalates produced from the different blends.

The Journal of Chromatography, 16 (of 1964) on page 216, describes two C9 alcohol mixtures containing respectively 36 and 24% of linear alcohols, the balance being branched molecules, of which 53 and 34% respectively of the branches are methyl branches.

Since their introduction in the middle of the 20th century, esters of branched $C_9$ alcohols have gained widespread use as plasticisers for PVC. PVC compounds prepared with phthalate esters of branched $C_9$-rich alcohols are used in many different market segments; these include electrical wire insulation, flexible vinyl flooring, vinyl coated wallpaper, vinyl shower curtains, synthetic leather, vinyl boat covers, vinyl swimming pool liners, vinyl stationary products such as notebook covers, and tarpaulins.

Esters of branched $C_9$-rich alcohols are preferred over esters prepared from 2-ethylhexanol, because when used in PVC compounds the $C_9$ esters yield performance advantages over the pure $C_8$ esters in improved extraction resistance to water, lower emissions during processing, lower specific gravity and improved low temperature flexibility. However these products require 1 to 3 degrees C. higher processing temperatures and slightly longer dry-blending times than comparable products based on the pure $C_8$ esters.

In accordance with Wadey et al, "The Nonyl Phthalate Ester and Its Use in Flexible PVC", Journal of Vinyl Technology, December 1990, Vol, 12, No 4, pp 209-211, there are currently known dinonyl or di-2-methyloctyl (alpha branched) phthalate esters, which are not yet commercially available. Other commercially available phthalates vary in their degree of branching. These include moderately branched phthalate esters (Jayflex® DINP); slightly branched esters (Palatinol® N, Vestinol® 9); highly branched esters (3,5,5-trimethyl-hexyl phthalate type); and linear $C_9$ phthalate esters (Jayflex® L9P, 70% n-nonyl, 30% various alpha branched disomers).

Although the $C_9$-rich esters offer advantages over the pure $C_8$ esters with lower emissions, the level of emission is often not acceptable for some end-users. For products used in the interior passenger compartments of automobiles, manufacturers often develop specifications for the maximum level of emissions which can be released as the automobile sits in the sun. These emissions can result in the development of a "fog" or "light-scattering-film" that condenses or forms on the inner side of the windscreen. Currently no pure $C_8$ phthalate esters and no branched $C_9$ phthalate esters can satisfy the specifications which require a maximal fog formation observed after 3 hours at 100° C. in a fog testing apparatus. To meet these performance criteria, phthalate esters of branched or linear $C_{10}$ and $C_{11}$ alcohols or phthalate esters based on the more expensive linear $C_9$ alcohols (such as Jayflex® L9P) or esters of trimellitic anhydride are used.

SUMMARY OF THE INVENTION

There is therefore a continuing need for alcohols which will enable the production of plasticisers with an improved balance of properties, in particular an improved combination of low volatility and low viscosity. The $C_{8-10}$-based, preferably $C_9$-rich, phthalate, trimellitate and adipate esters (e.g. branched $C_9$ phthalate, trimellitate and adipate esters) of the present invention which are formed from a particular $C_{8-10}$ alcohol mixture, preferably $C_9$-rich, unexpectedly pass the fog test. Accordingly, the phthalate, trimellitate and adipate esters of the present invention have low fogging properties which are highly desirable for use in automotive interior applications.

Phthalate esters prepared from the particular $C_{8-10}$ alcohol mixture according to the present invention can provide a PVC plasticiser which has all the performance advantages associated with conventional branched $C_9$ phthalate esters, while PVC formulations containing the plasticisers dry-blend faster, i.e. they process faster than corresponding formulations containing dioctyl phthalate. When compared to the use of other known branched phthalate esters as plasticisers for PVC, the phthalate esters according to the present invention provide an improved combination of properties including improved processing efficiency, better low temperature performance, lower emission release during processing, as well as lower emission release during the use of the shaped article made from the plasticised PVC (such as fogging). Thanks to the lower volatility, these phthalate esters also provide a lower contribution to the buildup of Semi-Volatile Organic Compounds (SVOCs) in indoor air. SVOCs are currently defined as compounds boiling in the range delimited by normal hexadecane (n-$C_{16}$) and up to $C_{40}$.

Benzoate esters of the particular $C_{8-10}$ alcohol mixture according to the present invention provide a lower contribution to the buildup of Volatile Organic Compounds (VOCs) in indoor air, as measured by the FLEC and Chamber Emission Test, as measured by ENV norm 13419, the VOC test being ENV 13419-3 and the FLEC and Chamber Emission test being ENV 13419-2. The benzoate esters also bring beneficial affects on the low temperature performance of the final flexible PVC article.

The present invention therefore provides a $C_{8-10}$ alcohol mixture comprising from 15 to 70 wt %, preferably from 18 to 65 wt %, more preferably from 21 to 60 wt %, most preferably from 26 to 58 wt %, unbranched molecules, the balance being branched molecules and having an average branchiness of at most 2.00 branches per molecule, at least 80% of the branches being methyl branches and at least 50 mol % of the branched molecules being mono-methyl branched.

DETAILED DESCRIPTION OF THE INVENTION

In a preferred embodiment, at least 75% by weight, more preferably at least 85% and most preferably 95% by weight of the mixture are $C_9$ alcohols.

In a yet further preferred embodiment, the balance of the alcohol mixture (ie the branched $C_8$-$C_{10}$ alcohol component of the mixture) has an average branchiness of at most 1.7 branches per molecule, more preferably from 1 to 1.5 and most preferably from 1 to 1.3 branches per molecule.

It is also preferred that the overall alcohol mixture has an average branchiness from 0.3 to 1.25 branches per molecule. That is to say, the branched and unbranched $C_8$-$C_{10}$ alcohol components of the mixture together have the specified average branchiness.

In another preferred embodiment at least 90 mol % of the branches in the balance (the branched component) are methyl branches and in a particularly preferred embodiment at least 97.5 mol % of the branches in the balance are methyl branches. In an especially preferred embodiment all the branches in the balance are methyl branches.

In a further preferred embodiment at least 75 mol % of the branched molecules are mono-methyl branched and in a particularly preferred embodiment at least 90 mol % of the branched molecules are mono-methyl branched. In an especially preferred embodiment at least 99 mole % of the branched molecules are mono-methyl branched.

In yet another preferred embodiment at most 5 mole % of the branched molecules in the mixture have their only branch (or in the case where there is more than one branch, their first branch) located on the third carbon atom in the molecule (counting from the hydroxyl group of the alcohol function). In this and other embodiment(s), the mixture may contain branched molecules where there is branching on the second carbon atom counting from the hydroxyl group and/or branching on a carbon atom beyond the third carbon atom counting from the hydroxyl group. Mixtures having a low proportion of molecules with their only (or their first) branch on the third carbon atom may be prepared, for example, by processes employing liganded rhodium catalysts at lower pressures.

The present invention also provides esters produced by the reaction of the $C_{8-10}$, preferably $C_9$-rich alcohols of the present invention with carboxylic acids and/or acid anhydrides. One such ester may be the ester with benzoic acid. In particular the invention provides esters of the alcohols of the present invention and polycarboxylic acids and anhydrides such as adipates, trimellitates, cyclohexane dicarboxylic acid esters, and especially phthalates. The invention further provides the use of such esters as plasticisers for plastics particularly polyvinyl chloride.

The alcohols of the present invention may be produced by hydroformylation of $C_{7-9}$ olefin mixtures, preferably octene rich mixtures, having the structure to produce the alcohol mixtures of the present invention. The olefins may be produced in any suitable manner. For example they may be synthesized or they may be separated out from other olefin containing mixtures. The unbranched and mono-methyl branched olefins may readily be obtained by Fischer-Tropsch synthesis from syngas, preferably employing an iron catalyst. Alternatively the olefins may be the residue after the extraction of n-octene-1 from octene-rich streams produced by Fischer Tropsch synthesis.

In another embodiment, octenes may be a mixture of unreacted octenes from ethylene/octene copolymerization to produce linear low density polyethylene (LLDPE) obtained as a byproduct stream rich in primarily unbranched octenes, a significant proportion of which are terminal olefins.

Such octene containing byproduct streams, for example originating from the solution process to produce LLDPE with octene-1 as a comonomer may still contain for example from 35 to 60% by weight of octene-1, preferably from 37 to 45%, more preferably around 40%, i.e. from 38 to 42% by weight. They will contain also linear internal octenes, such as octene-2, octene-3 and octene-4, which are present as a minor component in the comonomer feed, and also partly result from isomerisation during the LLDPE polymerisation reaction. The byproduct streams may therefore contain for example from 15 to 40% by weight of these linear internal octenes, preferably from 20 to 30% by weight, more preferably from 23 to 28% by weight. Also branched octenes may be present, primarily coming as a minor component in the comonomer feed to the polymerisation reaction. The byproduct streams may contain branched octenes in amounts similar to the linear internal octenes, and these branched octenes may primarily be monomethylheptenes. In addition, the byproduct streams may contain octanes, primarily n-octane, also originating from the comonomer feed, for example in levels from 1 to 4% by weight, such as 1 to 3% by weight.

The composition and structure of the alcohols of the present invention may be determined as follows.

The carbon number range of the alcohol mixture and the individual carbon number content of the mixture may be determined by capillary Gas Chromatography (GC), preferably a polar column, usually expressed in weight %. Standard industry practice is to split the GC spectrum into carbon number regions corresponding to the individual normal alcohols such as n-heptanol, n-octanol, n-nonanol and n-decanol. The region eluting before a particular normal alcohol but after the normal alcohol having one less carbon atom than that particular normal alcohol is assigned to the branched alcohols having the number of carbon atoms of the particular (higher) normal alcohol. For example, the GC region between n-octanol and n-nonanol, and the region including the n-nonanol, are considered to correspond to all the $C_9$ alcohols. This carbon number composition expressed in weight % may be readily converted into mole %.

The content of normal or unbranched alcohol molecules in weight % in a $C_{8-10}$ alcohol mixture may also be determined by capillary GC. The retention times for n-octanol, n-nonanol and n-decanol on the GC apparatus used for the analysis need to be established and the apparatus calibrated with appropriate standards.

The wt % of the normal alcohols in the sample may then be determined and the wt % may readily be converted to mole %. In cases where the resolution (e.g. peak separations) of a particular alcohol mixture on a particular GC apparatus is judged to be insufficient for enabling good identification of components, the resolution may need to be improved. This may be achieved, for example, by first silylating the alcohol mixture and applying a GCMS (Gas Chromatography Mass Spectrometry) technique to the silylated sample. However, for alcohol mixtures in the $C_8$-$C_{10}$ range, this more complex technique is usually not required, and straightforward GC measurements are sufficient.

In order to determine the average branchiness of the balance of the mixture, the average branchiness of the overall mixture is established first, using $^1$H-NMR. The effect of the proportion of unbranched material in the alcohol mixture, as established by GC, as above, is then calculated out, to give the average branchiness of the branched balance.

The average number of branches per molecule for the alcohol mixture is determined in $^1$H-NMR (using a 30% volume solution of the alcohol in deuterochloroform), employing the integration of the —$CH_3$ protons having chemical shifts relative to that of tetramethylsilane between 1 and 0.4 ppm and the integration of the —$CH_2O$-protons between 3.9 and 3 ppm. The dilution of the sample assures that the hydroxyl proton can be observed between 3 and 2 ppm.

With I representing the integral of a region, the average number of branches is $$((2*I_{(1-0.4\,ppm)})/(3*I_{(3.9-3\,ppm)}))-1$$

This calculated average number of branches per molecule assumes that none of the alcohol isomers contains any cycloalkyl structures. Such isomer structures are difficult to identify and in the above formula are neglected for convenience. In cases where such cycloalkyl alcohol structures are present in the mixture, they are typically in concentrations of less than 3 mole %, such as less than 2 mole % or less than 1 mole %. In such cases, fewer methyl protons will be detected for the entire mixture, so that the average number of branches will be somewhat underestimated using the above formula. The presence of cyclic structures, because of their lower H/C ratio compared to an equivalent non-cyclic structure, also affects the average carbon number (which can be derived from the $^1$H-NMR spectrum, if desired). These inaccuracies are typically neglected for convenience, and the analytical results are typically expressed and assumed as being for mixtures not containing any cyclic structures.

This average number of branches per molecule for the entire mixture may then be used to calculate the branchiness of the (branched) balance by taking into account the mole % of unbranched molecules derived from the previously described GC measurement.

$^{13}$C-NMR (using a 50% volume solution of the alcohol in deuterochloroform containing $Cr(acac)_3$ as a relaxation agent and tetramethylsilane as a reference) may be used to determine the percentage of molecules according to the location of the closest branch relative to the hydroxyl group of the alcohol function. Based on literature data and standard chemical shift calculations, position of the closest branch is indicated as follows:

a) first branch at C-2, C-4 and C-5+: between 72.3 and 62.0 ppm
b) first branch at C-3: between 62.0 and 58.0 ppm If desired, the first group may be further split into the individual elements, and also the 3,4-disubstituted isomers may be separated out.

The percentage of each type of material present can then be obtained by using the integral of the specified region for the specific material and the integral of the whole —CH$_2$OH- region between 74 and 56 ppm.

$$\text{Percentage of molecules branched at } X = 100 * I_{(region\ X)}/I_{(74\text{-}56\ ppm)}$$

If a more detailed compositional and structural analysis is required, $^{13}$C-NMR may be used. The analysis is more easy if the backbone structure of the feed olefins for the hydroformylation reaction used to produce the alcohols is known. This backbone structure may be determined by for example capillary GC analysis with on-line or in-situ hydrogenation of the feed olefins before they enter the GC column, a known technique also referred to hereinafter as "hydro-GC". Knowing the specifics of the hydroformylation reaction, one may then determine the specific alcohol structures to be expected in the mixture, and their relative proportions. $^{13}$C-NMR library data may be used for the chemical shift assignment of the projected species, or in absence thereof, chemical shifts for them may be calculated.

Further structural information may be derived by an additional NMR-experiment on the same solution as used for the $^{13}$C-NMR-measurement:

DEPT (Distortionless Enhancement through Polarization Transfer), generating separate spectra for the carbon atoms in respectively the methylene, methyl and methine fractions of molecules.

The data collected on expected isomers, their expected relative abundance and the chemical shifts of their characteristic fragments may then be used in conjunction with the $^{13}$C-NMR-spectra, and with the DEPT-spectra to show the different types of protonated carbon atoms present. The peaks in the spectrum indicating the major branch-systems may then be assigned.

This analysis enables the type of branches present and their relative abundance to be determined. Isolated methyl branches show up in the $^{13}$C-NMR-spectra at around 16-22 ppm, methyl groups in ethyl branches between 6 and 13 ppm, methyl groups in n-propyl or longer branches at around 14 ppm, overlapping with the terminal methyl groups.

A battery of two-dimensional NMR-experiments may also be used to generate extra spectral information concerning the environment of particular carbon atoms and in particular the number of protons they carry.

(1) GHSQC (Gradient Heteronuclear Single Quantum Coherence): showing single bond carbon-hydrogen connectivity: the correlation between carbons and the protons they are carrying.

(2) GHMBC (Gradient Heteronuclear Multiple Bond Coherence): showing multiple bond carbon-hydrogen connectivity: the correlation between carbons and protons on carbons further down the chain. The technique is more sensitive for the protons on the first two carbons in any direction.

(3) GHSQC/TOCSY (Gradient Heteronuclear Single Quantum Coherence/TOtal Correlation SpectroscopY): showing single bond carbon-hydrogen connectivity, and multiple bond hydrogen-hydrogen connectivity: the correlation between carbons and the protons they are carrying, while extending the proton correlation to the whole spin-system they take part in. This experiment is less sensitive than GHMBC.

Again the use of the information of the two-dimensional spectra, the one-dimensional spectra, the literature data and calculated chemical shifts, and making sure that all the different pieces of information match (connectivity, shifts, types of carbon, intensities), allows the peaks at lower intensity to be identified.

The alcohol manufacturing process can produce racemic mixtures of diastereoisomers. These then show up in the spectra as multiple peaks of the same height which are to be combined in the analysis to determine the total amount present of the specific isomer.

An approximate knowledge of the feed olefin isomer composition, such as the equivalent paraffin backbones determined by hydro-GC, allows a check to be made on the analytical result since the alcohol isomer mix must fit the olefin isomer mix, when the specifics of the hydroformylation reaction are taken into account, even allowing for a possible shift of the olefin bond before it is hydroformylated.

The isomers can be different either in number of branches (e.g. up to 3), branch length (e.g. up to 3 carbon atoms), or in position of the branch (proximity to the —CH$_2$OH-group, on the same backbone carbon atom or at different backbone carbon atoms).

Using the integral for a particular carbon atom of a particular isomer and the integral of the —CH$_2$OH-carbon between 74 and 56 ppm, the contribution of the isomer to the mixture composition can be calculated as follows.

$$\text{Mole percentage of isomer } X = 100 * I_{(carbon\ X)}/I_{(-CH2OH\ between\ 74\text{-}56\ ppm)}$$

The NMR results are typically expressed in molar percentages. Since the isomer identity is assembled from different molecular fragments, often the total carbon number of the particular isomer remains uncertain. Only in mixtures of a single carbon number, the full identity of the isomer can be stated for certain.

The isomers can be grouped together: for a particular type of branch, or at a particular position. As an ultimate test, the grouping of isomers should match the results previously obtained for:

a) the average degree of branching
b) the fraction of material according to the position of the branch nearest to the alcohol group
c) the feed backbone composition if available This entire identification and quantification process is only valid for the average molecular composition: it is difficult to link a branch-fragment to an isomer with a certain carbon number. Hence there can remain uncertainty to the exact carbon number of each of the identified isomers.

The alcohols are conveniently prepared by the hydroformylation of olefins, if necessary followed by hydrogenation and distillation. The hydroformylation typically uses a homogeneously dissolved catalyst complex, which may be based on cobalt or rhodium. Ligands may be used to modify the catalyst complex, usually being phosphorus based, and tributylphosphine is typically known to be used with cobalt metal. With rhodium, the ligands are typically organophosphines, with triphenylphosphine (TPP) being preferred, or organophosphites. Organophosphite ligands can be those disclosed in U.S. Pat. Nos. 4,599,206, 4,668,651, 4,737,588, 4,748,261, 4,769,498, 4,774,361, 4,789,753, 4,835,299, 4,871,880, 4,885,401, 5,179,055, 5,288,918, 5,312,996, 5,364,950, 5,681,473, 5,756,855, and WO 97/20793. Preferred is 6,6'-[[3,3',5,5'-tetrakis(1,1-dimethylethyl)-1,1'-biphenyl-2,2'-diyl]bis(oxy)]bis-dibenzo [d,f] [1,3,2]-dioxaphosphepin, or 6,6'-[[3,3',5,5'-tetrakis(1,1-dimethylpropyl)-1,1'-biphenyl-2,2'-diyl]bis(oxy)]bis-dibenzo [d,f] [1,3,2]-dioxaphosphepin, or 6,6'-[[3,3'-bis(1,1-dimethylethyl)-5,5'-dimethoxy[1,1'-biphenyl]-2,2'-diyl]bis(oxy)]bis-dibenzo [d,f] [1,3,2]-dioxaphosphepin, or tris(2,4,6-di-t-butylphenyl)-phosphite. Most preferred is 6,6'-[[3,3',5,5'-tetrakis(1,1-dimethylethyl)-1,1'-biphenyl-2,2'-diyl]bis(oxy)]bis-dibenzo [d,f] [1,3,2]-dioxaphosphepin. Ionic varieties of such phosphites are disclosed in U.S. Pat. Nos. 5,059,710 and 5,113,022.

Certain of these hydroformylation catalyst complexes, for example rhodium with TPP, have a tendency to preferentially react terminal olefins, and also to reduce or even essentially prevent the hydroformylation of the specific terminal olefins that have a branch on the beta carbon, i.e. the second carbon counting from the end with the double bond. As a result, the product alcohol mixture may contain little to no alcohol isomers that have a first branch on the third carbon, counting from the end with the alcohol function. Under these circumstances the alcohol mixture of this invention will comprise at most 5 mole %, preferably at most 3 mole %, more preferably at most 1.5 mole %, even more preferably at most 1.0 mole %, and most preferably at most 0.5 mole % of branched molecules having their first branch located on the 3rd carbon atom counting from the hydroxyl group of the alcohol function. Since these hydroformylation catalyst complexes allow operation at low pressure and temperature, the alcohol mixtures according to this particular embodiment are relatively easy to produce. Molecules with branching at the second carbon, or with their first branch at carbon atoms beyond the third carbon counting from the hydroxyl group of the alcohol function may occur in higher abundancies in these mixtures.

When a C8-C 10 alcohol mixture is produced by hydroformylation of an octene containing byproduct stream from an LLDPE process, and using rhodium and TPP as a ligand of the hydroformylation catalyst system, the resulting alcohol will typically contain at least 95% by weight of C9 alcohols, preferably at least 98%. It will typically contain from 50 to 70% by weight of unbranched alcohol molecules, preferably from 60 to 65% by weight. The average branchiness of all alcohol components of the mixture together will typically be from 0.3 to 0.6 branches per molecule, preferably from 0.35 to 0.45. The fraction of the composition that constitutes the branched component will have an average branchiness from, for example, 1.0 to 1.5, preferably from 1.0 to 1.2, more preferably from 1.0 to 1.1. At least 80% of the branches typically will be methyl branches, preferably at least 90%, more preferably even at least 95%. Of the branched molecules, typically at least 75% will be mono-methyl branched, preferably at least 85%, more preferably at least 90%.

Alternatively, when unliganded cobalt is used as the hydroformylation catalyst on such byproduct streams, the resulting alcohol may typically contain from 40 to 60% by weight of unbranched alcohol molecules, preferably from 47 to 55%. The average branchiness of all alcohol components of the mixture together will typically be from 0.4 to 0.8 branches per molecule, preferably from 0.5 to 0.65. The fraction of the composition that constitutes the branched component will have an average branchiness from, for example, 1.0 to 1.5, preferably from 1.0 to 1.2, more preferably from 1.0 to 1.1. With this cobalt catalyst type, the proportion of methyl branches is typically lower than with the above-liganded rhodium catalysed processor. The proportion will generally be at least 70% of the branches, but typically not more than 90%. Preferably from 75 to 85% of the branches may be methyl branches. Of the branched molecules, typically from 50% to 70% will be mono-methyl branched, preferably from 60 to 65%.

When the composition of the olefin feed is known to comprise relatively low amounts of normal and/or branched alpha olefins, as compared to internal olefins, in order to produce the alcohol mixtures of the present invention it may be preferred to use a hydroformylation catalyst system capable of double bond isomerisation, such as the cobalt-based systems, or the systems based on the phosphite ligands mentioned above. The alcohol mixtures produced with these systems will tend to contain higher amounts of unbranched molecules and/or higher amounts of mono-methyl branched molecules, which are more desired.

The conditions for performing the hydroformylation reaction, and any further purification of the hydroformylation product, depend on the catalyst system used and are well known standard techniques and conditions. For example, techniques such as hydrogenation and/or distillation may be used for the purification and separation of the hydroformylation product, and for the isolation of the desired alcohol mixture.

The esters of the present invention are prepared by esterification of acids and/or their anhydrides with the $C_{8-10}$, preferably $C_9$-rich alcohols of the invention.

The esterification process comprises the following steps: a) adding the acid and/or anhydride and an excess of the alcohols to a reaction vessel and b) heating the reaction mixture to a temperature at about or above the boiling point of the alcohol and maintaining a pressure sufficient to obtain boiling of the reaction mixture. The acid and/or anhydride and the alcohols are thereby converted to an ester. Water and the unreacted alcohol are removed from the reaction vessel and the alcohol removed may be recycled to the vessel.

The esterification process is preferably conducted in the presence of a catalyst. Typical esterification catalysts of commercial importance are sulfuric acid, methane sulfonic acid (MSA), para-toluene sulfonic acid (pTSA), stannous alcoholates or oxides, and titanium alcoholates. U.S. Pat. No. 3,056,818 discloses titanium esterification catalysts and is incorporated herein by reference, the more commonly used catalysts being tetra-isopropyl titanate, any of the tetra-butyl titanates, and/or tetra-octyl titanate. More details on how the esterification process may be conducted, may be found in U.S. Pat. Nos. 5,324,853, 5,880,310 and 6,355,817, or in copending United Kingdom patent application No 0320206.6, which are incorporated herein by reference.

The esterification process may further include one or more of the following steps: removing excess alcohol by nitrogen or steam stripping; adding adsorbents such as alumina, silica gel, activated carbon, clay and/or filter aid to the reaction mixture following esterification before further treatment; adding water and base to simultaneously neutralise the residual organic acids and to hydrolyse the catalyst (if present); filtering off solids from the ester mixture containing the bulk of the excess alcohol; removing water by flashing or steam or nitrogen stripping under vacuum and recycling of the alcohol or acid into the reaction vessel; and removing solids from the stripped ester in a final filtration.

In certain cases adsorbent treatment may occur later in the process following steam stripping. In other cases, the adsorbent treatment step may be eliminated from the process altogether.

Although the alcohols of this invention are particularly useful in the production of plasticiser ester, they may be esterified with a wide range of acids. Phosphate esters may for example be produced, for use as flame retardants or as hydraulic fluids. Sulphates may be produced, for use as surfactants or surface active ingredients or as plasticisers. Carboxylic acids which undergo esterification (i.e. mono or polybasic acids, preferably dibasic or tribasic acids) with alcohols can be aliphatic, cyclo-aliphatic or aromatic, they can be substituted or unsubstituted, saturated or unsaturated, or they can be blends of acids. Representative acids include acetic, propionic, lactic, n-butyric, isobutyric, n-valeric, isovaleric, n-heptanoic, caproic, pelargonic, carprylic, lauric, palmitic, malonic, succinic, adipic, azelaic, sebacic, citric, acrylic, methacrylic, undecylenic, oleic, linoleic, maleic, fumaric, myristic, stearic, isostearic, branched $C_5$, $C_6$, $C_7$, $C_8$, $C_9$, $C_{10}$, $C_{11}$, $C_{12}$ and $C_{13}$ oxo-acids (e.g. 3,5,5-trimethylhexanoic acid), and branched $C_{16}$, $C_{18}$, $C_{20}$, $C_{24}$, $C_{26}$, $C_{28}$, $C_{32}$, $C_{36}$, $C_{40}$, $C_{44}$, $C_{48}$ acids derived using the Guerbet reaction and oxidation. Acetates may be used as solvents or as fragrance components.

Among the alicylic acids that may be esterified are cyclopentane carboxylic, cyclohexane carboxylic, cycloheptane carboxylic, or 1,2-, 1,3- or 1,4-cyclohexane dicarboxylic acids. The aromatic acids include benzoic acid, substituted benzoic acids, phthalic, isophthalic, terephthalic, benzene-1,2,4-tricarboxylic, pyromellitic acids and acids of naphthalenes. Anhydrides of mono and polybasic acids can be used in place of the acids, especially when plasticiser esters are being formed. Important anhydrides are maleic anhydride, phthalic anhydride, trimellitic anhydride and pyromellitic anhydride. Important esters therefore are benzoates, adipates, trimellitates, cyclohexanoates, particularly dicyclohexanoates, and phthalates.

The performance as plasticiser in a PVC compound of phthalate esters derived from the alcohol mixtures of the invention is further illustrated in Tables 1 and 2, where (Table 2) it is compared to three commercially available phthalate esters Jayflex® DINP, Palatinol® N and Jayflex® L9P. Table 1 gives the composition and structure of the alcohols upon which the commercial phthalate esters are based and the predicted composition of a product of the invention.

TABLE 1

| Phthalate ester: | Jayflex DINP | Palatinol N | Jayflex L9P | Invention |
|---|---|---|---|---|
| Capillary GC (wt %) | | | | |
| Unbranched molecules | <1 | 3.6 | 68.9 | 65 |
| ≦C8 alcohols | 3 | <1 | 0.9 | 1 |
| C9 alcohols | 72 | >96 | 99 | 98 |
| ≧C10 alcohols | 25 | <3 | 0.1 | 1 |
| $^1$H NMR | | | | |
| Avge Carbon No | 9.3 | 9.12 | 9.11 | 9.0 |
| Avge No of branches/molecule | 2.1 | 1.50 | 0.33 | 0.5 |
| Avge branchiness of the balance | 2.1 | 1.56 | 1.07 | 1.43 |
| $^{13}$C NMR (mole %) | | | | |
| First branch at C-2 | 11.4 | 19.2 | 29.0 | 7.4 |
| First branch at C-3 | 32.5 | 10.5 | 0.97 | 0.1 |
| 3,4-disubstituted | 16.2 | 6.0 | 0.0 | 0.0 |
| First branch at C-4 | 24.6 | 45.9 | 0.49 | 12.0 |
| First branch at C-5+ or no branch | 15.3 | 18.4 | 69.54 | 80.5 |
| Total | 100.0 | 100.0 | 100.0 | 100.0 |
| % of branches being methyl | 95 | 87 | 69.0 | 100 |
| % of branched molecules being mono-methyl branched | 19 | 41 | 64.3 | 70 |

TABLE 2

| Phthalate ester: | Compound 1 Jayflex DINP | Compound 2 Palatinol N | Compound 3 Jayflex L9P | Compound 4 This Invention * |
|---|---|---|---|---|
| % unbranched | 0 | <5 | 68.9 | 65 |
| Avge branchiness of the balance | 2.1 | 1.56 | 1.07 | 1.43 |
| % branches being methyl | 95 | 87 | 69 | 100 |
| % branches, non-methyl | 5 | 13 | 31 | 0 |
| % of branched molecules being mono-methyl branched | 19 | 41 | 64 | 70 |
| Physical Property | | | | |
| Shore A Hardness | 90 | 89 | 89 | 88 |
| Shore D Hardness | 39 | 39 | 36 | 36 |
| 100% Modulus (N/mm^2) | 16 | 15 | 15 | 15 |
| Tensile Strength (N/mm^2) | 23 | 23 | 23 | 23 |
| Elongation | 304 | 338 | 317 | 310 |
| Breaking Energy (Joule) | 18.0 | 19.4 | 17.4 | 17.4 |
| Clash - Berg (Tf) | −11.8 | −13.5 | −21.6 | −23.0 |
| Brittleness (Tb) | −23.4 | −26.4 | −32.7 | −33.0 |
| Retained Tensile (%) | 99 | 97 | 98 | 98 |
| Retained Modulus (%) | 109 | 109 | 109 | 108 |
| Retained Elongation (%) | 86 | 83 | 95 | 97 |
| Weight Loss (%) | 4.8 | 3.7 | 3.0 | 2.8 |
| Compound Specific Gravity | 1.2446 | 1.2447 | 1.2426 | 1.2412 |
| Fogging, 100 C., 3 hrs (% reflectancy) | 62 | 65 | 77 | 82 |

* predicted using the COPPCO database, as described in U.S. Pat. No. 6,355,711.

The properties are given for the formulation: PVC 100, plasticizer 40, stabilizer 2, stearic acid 0.25. The PVC resin is a suspension grade with a K71 molecular weight index currently marketed under the tradename Oxy 240.

Particular performance benefits are predicted for compound 4 of the invention in the low temperature performance (as indicated by the Clash—Berg test), in reduced % weight loss and in the fogging performance. Also the lower predicted compound specific gravity brings volume/cost efficiency advantages in the production of flexible PVC articles, in that products having the same volume and comparable properties can be obtained using less weight of raw materials.

Many of the esters derived from the alcohols of the present invention are also useful as lubricant components and as ingredients of synthetic lubricants.

Other derivatives of interest from the alcohols of the invention are useful in the field of surfactants and detergents, emulsifiers and the like. These derivatives include sulphates, alkoxylates such as ethoxylates or propoxylates or EO/PO block copolymers, the latter being useful as non-ionic surfactants. Some of these alkoxylates, preferably those with only a few, such as 2, 3 or 4 alkoxy molecules incorporated, may also be sulphated to the corresponding alkoxysulphates, which can also be used as ionic surfactant molecules. Typically these ionic surfactant molecules are used as the salt of an alkali metal such as sodium or potassium, or a salt of a metal. The use of the alcohols of the present invention provide the benefit of improved biodegradation due to a low content of quaternary carbon atoms, as well as a low content of molecules with more than one branch. The presence of quaternary carbon atoms, and two or more branches in a molecule and in specific positions relative to each other, are known to impede biodegradation of the alkyl chain of the molecule, and hence molecules containing these groups are less preferred in the surfactant industry.

Yet further derivatives of interest from the alcohols of the invention include Guerbet alcohols, which may be derived by performing the Guerbet reaction on the alcohols, and which are characterised by having twice the carbon number of the starting alcohols, i.e. C16-C20, preferably C18, and having a branch on the 2 position to the hydroxyl group. Further derivatives of these Guerbet alcohols may be esters such as sulfates or phosphates, ethers such as alkoxylates, and alkoxysulphates or alkoxyphosphates. These derivatives will also enjoy the benefit of high biodegradability because of the typical absence of quaternary carbon atoms, and in addition have the benefits of low volatility due to the higher carbon number, and low pour point because of the branched alkyl structure.

The invention claimed is:

1. A mixture comprising branched primary alcohols having from 8 to 10 carbon atoms and unbranched primary alcohols having from 8 to 10 carbon atoms, which mixture comprises from 21 to 60 wt % unbranched molecules, the balance being branched molecules and having an average branchiness of at most 2.00 branches per molecule, at least 80% of the branches being methyl branches and at least 75 mole % of the branched molecules being mono-methyl branched, said mixture further characterized in that at most 5 mole % of branched molecules have a branch located on the third carbon atom counting from the hydroxyl group of the alcohol function, said mixture produced by the hydroformylation of $C_7$-$C_9$ olefins and if necessary followed by hydrogenation.

2. The mixture according to claim 1 comprising at least 75% by weight of $C_9$ alcohols.

3. The mixture according to claim 2 comprising at least 95% by weight of $C_9$ alcohols.

4. The mixture according to claim 1 wherein the branched $C_8$-$C_{10}$ alcohol component of the mixture has an average branchiness of from 1 to 1.5 branches per molecule.

5. The mixture according to claim 1 wherein the branched and unbranched $C_8$-$C_{10}$ alcohol components of the mixture together have an average branchiness of from 0.3 to 1.25 branches per molecule.

6. The mixture according to claim 1, produced by the hydroformylation of octenes.

7. The mixture according to claim 1, wherein the $C_7$-$C_9$ olefins are formed by Fischer-Tropsch synthesis.

8. The mixture according to claim 1, wherein the $C_7$-$C_9$ olefins comprise an unreacted stream from a linear low density polyethylene production process.

9. The mixture according to claim 1, wherein at least 90 mole % of the branched molecules are mono-methyl branched.

10. The mixture according to claim 1, wherein at least 99 mole % of the branched molecules are mono-methyl branched.

11. The mixture according to claim 1, said mixture produced by the hydroformylation of olefins using a rhodium catalyst.

* * * * *